US012251218B2

(12) United States Patent
Avirovikj et al.

(10) Patent No.: US 12,251,218 B2
(45) Date of Patent: Mar. 18, 2025

(54) BASE UNITS, TRANSMITTER UNITS, WEARABLE DEVICES, AND METHODS OF CONTINUOUS ANALYTE MONITORING

(71) Applicant: Ascensia Diabetes Care Holdings AG, Basel (CH)

(72) Inventors: Dragan Avirovikj, Stamford, CT (US); Igor Y. Gofman, Croton-on-Hudson, NY (US); Cameron M. Young, Tarrytown, NY (US); Ji Li, Wayne, NJ (US); Thomas A. J. Mayer, Jr., Glenmoore, PA (US)

(73) Assignee: Ascensia Diabetes Care Holdings AG, Basel (CH)

( * ) Notice: Subject to any disclaimer, the term of this patent is extended or adjusted under 35 U.S.C. 154(b) by 316 days.

(21) Appl. No.: 17/581,839

(22) Filed: Jan. 21, 2022

(65) Prior Publication Data
US 2022/0231526 A1    Jul. 21, 2022

Related U.S. Application Data

(60) Provisional application No. 63/140,083, filed on Jan. 21, 2021.

(51) Int. Cl.
*A61B 5/145*    (2006.01)
*A61B 5/00*    (2006.01)

(52) U.S. Cl.
CPC ........ *A61B 5/14532* (2013.01); *A61B 5/0002* (2013.01); *A61B 5/14503* (2013.01);
(Continued)

(58) Field of Classification Search
CPC .............. A61B 5/14532; A61B 5/0002; A61B 5/14503; A61B 5/6802; A61B 5/6848; A61B 2560/0214
(Continued)

(56) References Cited

U.S. PATENT DOCUMENTS

2004/0215958 A1* 10/2004 Ellis ........................ H04W 4/80
713/155
2014/0316223 A1    10/2014 Heck et al.
(Continued)

FOREIGN PATENT DOCUMENTS

EP    3632317 A1    4/2020

OTHER PUBLICATIONS

PCT Patent Application PCT/EP2022/051306 Notification of Transmittal of the International Preliminary Report on Patentability issued Mar. 3, 2023.
(Continued)

*Primary Examiner* — Gary F Paumen
(74) *Attorney, Agent, or Firm* — Erise IP, P.A.

(57) ABSTRACT

A base unit of a wearable device for continuous analyte monitoring includes a cup configured to receive a power source. A first power source contact is at least partially located in the cup and configured to electrically contact a first terminal of the power source in response to the power source being received in the cup. At least one base contact is electrically coupled to the first power source contact, the at least one base contact configured to electrically contact at least one transmitter contact of a transmitter unit in response to the transmitter unit and the base unit being coupled together. Numerous other embodiments are provided.

26 Claims, 11 Drawing Sheets

(52) U.S. Cl.
CPC .......... *A61B 5/6802* (2013.01); *A61B 5/6848* (2013.01); *A61B 2560/0214* (2013.01)

(58) Field of Classification Search
USPC ........................................................ 600/365
See application file for complete search history.

(56) References Cited

U.S. PATENT DOCUMENTS

| | | |
|---|---|---|
| 2017/0188910 A1 | 7/2017 | Halac et al. |
| 2017/0290546 A1 | 10/2017 | Antonio et al. |
| 2019/0336049 A1 | 11/2019 | Shah et al. |
| 2020/0196919 A1* | 6/2020 | Rao .................... A61B 5/14546 |

OTHER PUBLICATIONS

PCT Patent Application PCT/EP2022/051306 International Search Report and Written Opinion issued May 12, 2022.
European Patent Application 22703300.8 Office Action issued Feb. 4, 2025.

* cited by examiner

BASE UNITS, TRANSMITTER UNITS, WEARABLE DEVICES, AND METHODS OF CONTINUOUS ANALYTE MONITORING

CROSS REFERENCE TO RELATED APPLICATION

This claims the benefit of U.S. Provisional Patent Application No. 63/140,083, filed Jan. 21, 2021, the disclosure of which is hereby incorporated by reference herein in its entirety for all purposes.

FIELD

Embodiments of the present disclosure relate to continuous analyte monitoring apparatus and methods thereof.

BACKGROUND

Continuous analyte monitoring, such as continuous glucose monitoring (CGM), has become a routine monitoring operation, particularly in diabetes care. CGM provides real-time analyte (e.g., glucose) concentrations to users and/or medical professionals. By monitoring real-time glucose concentrations, therapeutic actions may be applied in a more timely fashion and glycemic conditions may be better controlled.

During a CGM operation, a wearable device is attached to a user and a biosensor of the wearable device is inserted subcutaneously. The biosensor is continuously operated in an environment surrounded by tissue and interstitial fluid and generates a signal that is indicative of the user's blood glucose concentration. This signal or the indication of the blood glucose concentration is transmitted to an external device, such as a reader, smart phone, or computer.

The wearable device receives power from an internal power source, such as a battery, which limits the lifespan of the wearable device. Thus, improved wearable devices are sought.

SUMMARY

In some embodiments, a base unit of a wearable device of a continuous analyte monitoring system is provided. The base unit includes a cup configured to receive a power source; a first power source contact at least partially located in the cup and configured to electrically contact a first terminal of the power source in response to the power source being received in the cup; and at least one base contact electrically coupled to the first power source contact, the at least one base contact configured to electrically contact at least one transmitter contact of a transmitter unit in response to the transmitter unit and the base unit being coupled together.

In some embodiments, a transmitter unit of a wearable device of a continuous analyte monitoring system is provided. The transmitter unit includes a recess configured to at least partially receive a battery in response to the transmitter unit and a base unit being coupled together, the battery supplying all power to the transmitter unit.

In some embodiments, a wearable device of a continuous analyte monitoring system is provided. The wearable device includes a base unit including: a cup; a power source received in the cup; a power source contact at least partially located in the cup and electrically contacting a terminal of the power source; and one or more one base contacts electrically coupled to the first power source contact. The wearable device also includes a transmitter unit including one or more transmitter contacts electrically contacting the one or more base contacts.

In some embodiments, a method of manufacturing a base unit of a wearable device of a continuous analyte monitoring system is provided. The method includes forming a cup configured to receive a power source; locating a power source contact at least partially in the cup, the power source contact configured to electrically contact a terminal of the power source in response to the power source being received in the cup; and electrically coupling at least one base contact with the power source contact, the at least one base contact configured to electrically contact at least one transmitter contact of a transmitter unit in response to the transmitter unit and the base unit being coupled together.

Other features, aspects, and advantages of embodiments in accordance with the present disclosure will become more fully apparent from the following detailed description, the claims, and the accompanying drawings by illustrating a number of example embodiments. Various embodiments in accordance with the present disclosure may also be capable of other and different applications, and its several details may be modified in various respects, all without departing from the scope of the claims and their equivalents. Accordingly, the drawings and descriptions are to be regarded as illustrative in nature, and not as restrictive.

BRIEF DESCRIPTION OF THE DRAWINGS

The drawings described below are for illustrative purposes and are not necessarily drawn to scale. The drawings are not intended to limit the scope of the disclosure in any way. Accordingly, the drawings are to be regarded as illustrative in nature, and not as restrictive.

DETAILED DESCRIPTION

Figure 1:
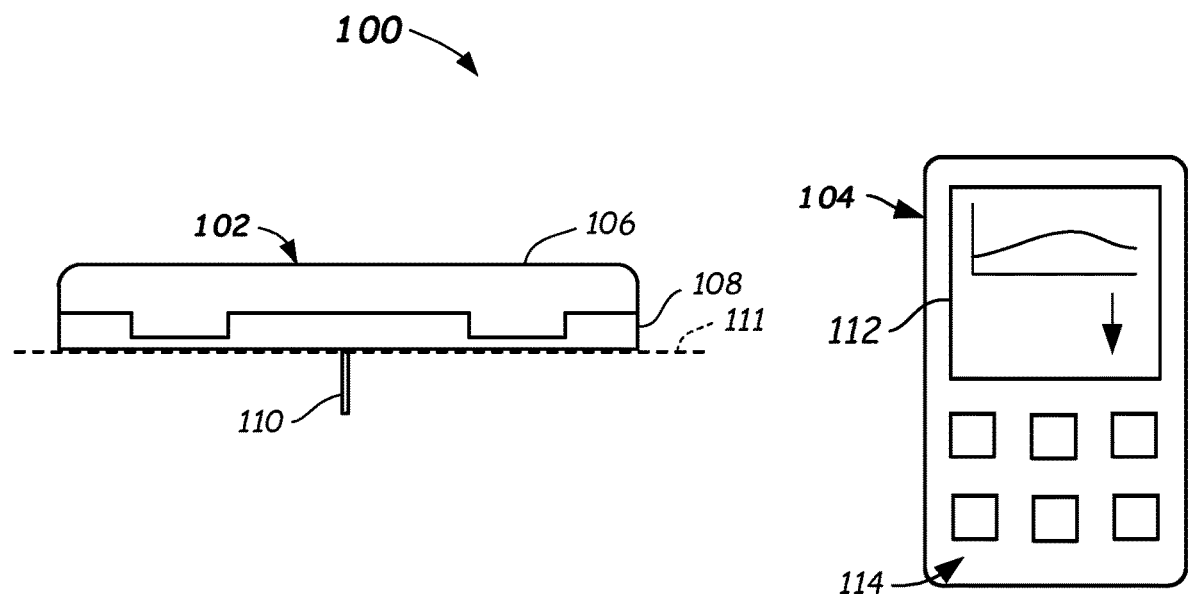
FIG. 1 illustrates a continuous analyte monitoring system including a side elevation view of a wearable device and a front view of an external device in accordance with one or more embodiments.

In order to more closely monitor analyte concentrations (e.g., glucose concentration) in people and detect changes in such analyte concentrations, methods and apparatus for continuous analyte monitoring (e.g., continuous glucose monitoring (CGM)) have been developed.

Some CGM systems have a wearable portion (a "wearable device") that is worn on the body and that can communicate (e.g., wirelessly) with an external device, such as a handheld receiver (reader) or another portable device, such as a smart phone with a suitable application software program. The wearable device may be worn for several days or even several weeks before being removed and replaced. The wearable device includes a biosensor that measures analytes, such as glucose in subcutaneous fluid. In some embodiments, the biosensor may be inserted with the assistance of a trocar or other device (also referred to as an insertion portion) that is inserted along with the biosensor subcutaneously, and then removed leaving the biosensor implanted. The wearable device may include circuitry coupled to the biosensor and configured to electrically bias the biosensor and measure current signals generated by the implanted biosensor. The wearable device may also include processing circuitry that determines analyte (e.g., glucose) concentrations based on the measured current signals, as well as electronic transmitter circuitry for communicating analyte (e.g., glucose) concentrations to the external device.

The wearable device of a CGM system is generally worn for up to several weeks and then is removed and replaced with a new wearable device. Having to replace the wearable device of a CGM system every few weeks can significantly increase the cost of performing continuous analyte monitoring. In general, the biosensor may need to be replaced, but other wearable device components can be reused many times, or even indefinitely. However, one of the factors limiting the use of the other components is the lifespan of a power supply that powers the components.

The wearable devices disclosed herein include reusable transmitter units that may use replaceable base units. For example, one or more power sources may be located within a replaceable base unit that interfaces and supplies power to a reusable transmitter unit. Thus, the wearable devices are provided with a fresh power supply every time the base unit is replaced. The wearable devices, methods, and systems disclosed herein provide users with a truly reusable transmitter unit without requiring recharging of power sources. In addition, the wearable devices disclosed herein avoid any fire hazards that may be associated with rechargeable batteries. Using a fresh power source(s) every time a new base unit is coupled to a transmitter unit prevents long term interruptions with the wearable devices. For example, use of the wearable device is not interrupted during recharging periods. In addition to the above-described advantages, the wearable devices disclosed herein enable more flexible, space-optimized transmitter units that can have different advantages. For example, the space where a power source would otherwise be located can be utilized for additional components such as sensors, accelerometers, etc., and/or the overall size of the transmitter units can be made much smaller.

Both the base unit and transmitter unit of a wearable device may be powered by the one or more power sources located in the base unit. In some embodiments, the transmitter unit provides an entire top portion of the wearable device and the coupling of the transmitter unit and the base unit together may retain the power source in a predetermined fixed location. In some embodiments, one or more of the power sources is located within a pocket in the base unit wherein a conductor configured as a spring mechanism retains the power source within the pocket. In some embodiments, one or more conductors on the transmitter unit may directly connect to one or more terminals of one or more power sources when the transmitter unit and the base unit are coupled together. These and other embodiments and methods are disclosed herein with reference to FIGS. 1-11.

The description below is described primarily with regard to continuous glucose monitoring, however, the apparatus and methods described below may be readily adapted to monitoring other analytes, such as cholesterol, lactate, uric acid, alcohol, and other analytes, in other continuous analyte monitoring systems.

Reference is now made to FIG. 1, which illustrates a continuous analyte monitoring system 100 including a side elevation view of a wearable device 102 and a front view of an external device 104. The wearable device 102 and the external device 104 may be in communication with each other, such as through wireless communication. The wearable device 102 includes a transmitter unit 106 and a base unit 108 that are physically and electrically coupled together. The transmitter unit 106 includes electronic components that enable communications, such as wireless communications, with the external device 104. The transmitter unit 106 may include other electronic components as described herein. The base unit 108 includes a biosensor 110 that measures one or more analytes. In the embodiment of FIG. 1, the biosensor 110 is shown implanted in or below skin 111 of a user. The biosensor 110 may be implanted using a trocar or other insertion tool (not shown, also referred to as an insertion portion). In the embodiments described herein, the analyte is glucose, but the devices, apparatus, and methods may be configured to measure other analytes as described herein. As described in greater detail herein, the base unit 108 also includes a power source (not shown in FIG. 1) that provides power to the base unit 108 and the transmitter unit 106.

The external device 104 may receive and/or transmit data and/or instructions to and/or from the wearable device 102. In some embodiments, the external device 104 may be a cellular telephone or other portable device. In other embodiments, the external device 104 may be a computer or a server. In some embodiments, the external device 104 may be located in a medical professional office or the like. The external device 104 may include a display 112 that displays information to a user, such as analyte concentrations (e.g., glucose concentrations). In addition, the external device 104 may include input devices 114, such as buttons, that enable a user to input information into the external device 104. In some embodiments, the external device 104 may process data generated by the wearable device 102 to calculate and/or display glucose concentrations.

Figure 2D:
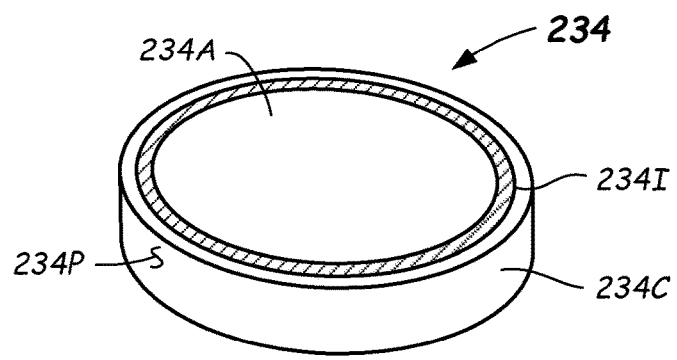
FIG. 2D illustrates a top isometric view of a battery used in a wearable device of a continuous analyte monitoring system in accordance with one or more embodiments.
Figure 2A:
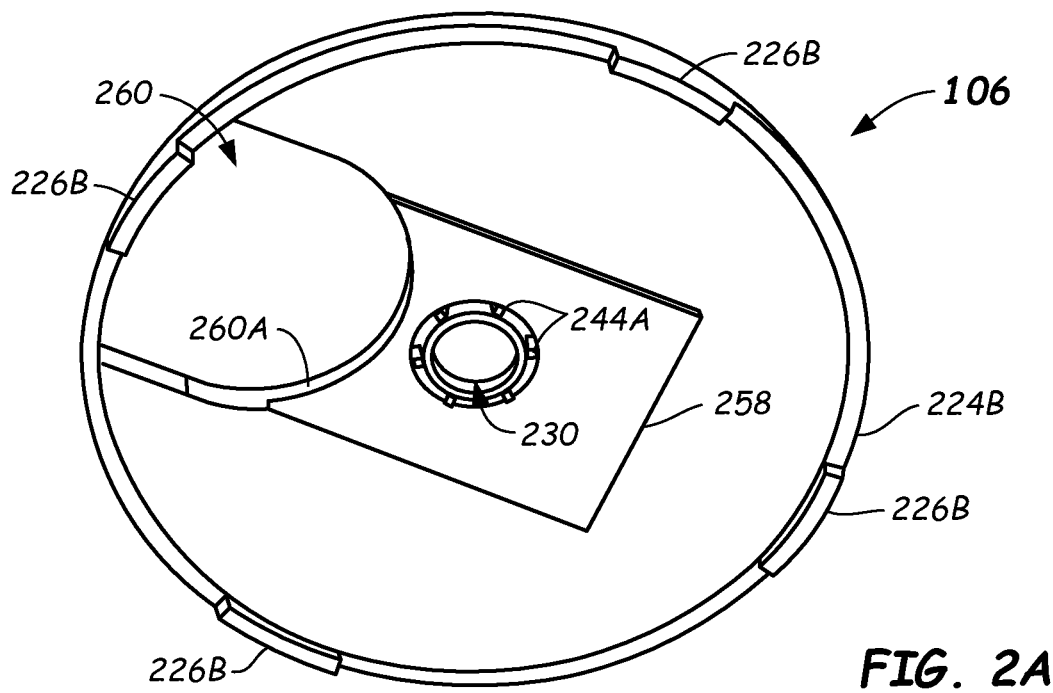
FIG. 2A illustrates a bottom isometric view of a transmitter unit of a wearable device of a continuous analyte monitoring system in accordance with one or more embodiments.
Figure 2B:
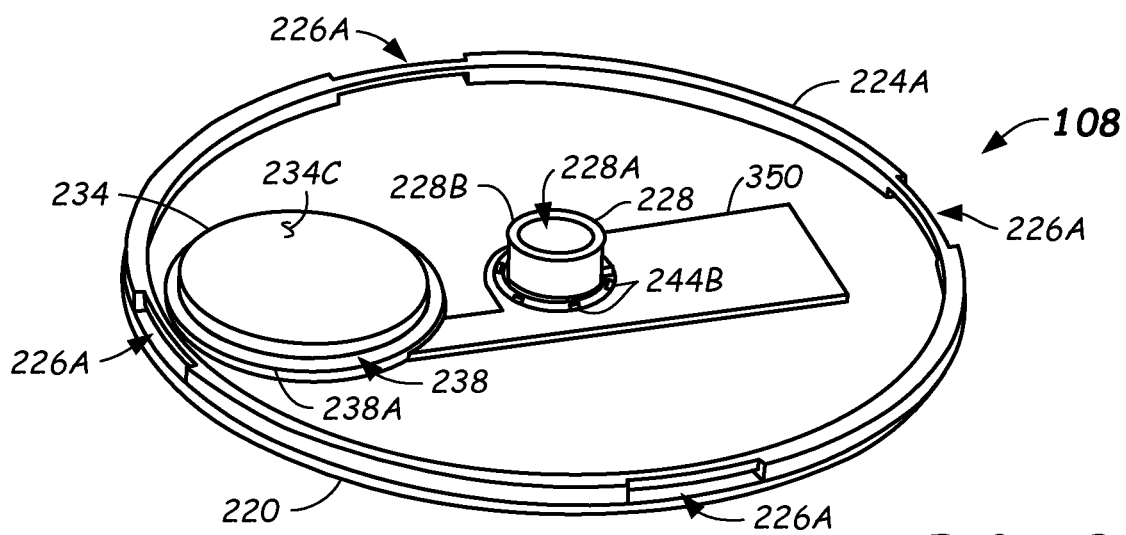
FIG. 2B illustrates a top isometric view of a base unit of a wearable device of a continuous analyte monitoring system in accordance with one or more embodiments.
Figure 2C:
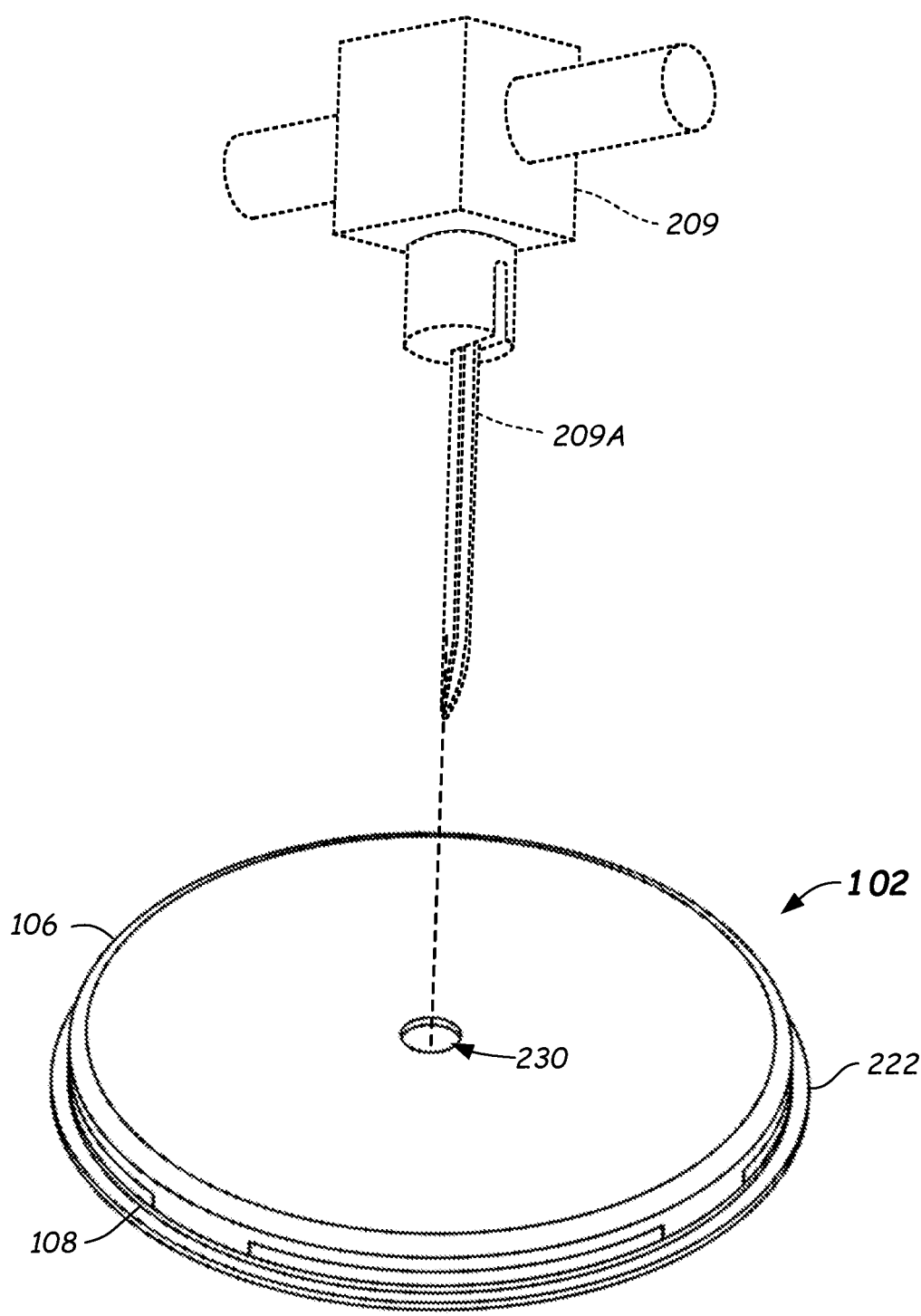
FIG. 2C illustrates a top isometric view of a wearable device of a continuous analyte monitoring system with a transmitter unit and a base unit coupled together in accordance with one or more embodiments.

Additional reference is now made to FIGS. 2A-2C. FIG. 2A illustrates a bottom isometric view of an embodiment of the transmitter unit 106 of the wearable device 102 (FIG. 2C). FIG. 2B illustrates a top isometric view of an embodiment of the base unit 108 of the wearable device 102 (FIG. 2C). FIG. 2C illustrates a top isometric view of an embodiment of the wearable device 102 with the transmitter unit 106 and the base unit 108 coupled together and an inserter assembly 209 configured to engage the wearable device 102.

The base unit 108 may include a baseplate 220 onto which components of the base unit 108 may be attached. In the embodiment of FIGS. 2A-2C, the baseplate 220, the base unit 108, the transmitter unit 106, and the wearable device 102 are round in plan view. The baseplate 220, the base unit 108, the transmitter unit 106, and the wearable device 102 may have other shapes, such as rectangular or oval. An adhesive layer 222 may be attached to the underside of the wearable device 102 and serves to adhere or otherwise attach the wearable device 102 to a user. For example, the adhesive layer 222 may attach the wearable device 102 to skin of a user when the biosensor 110 is implanted subcutaneously.

The baseplate 220 may include a base retainer ring 224A that is configured to mechanically couple to a transmitter retainer ring 224B attached to the transmitter unit 106 so as to mechanically couple the base unit 108 and the transmitter unit 106 together. In the embodiment of FIG. 2B, the base retainer ring 224A may be circular and may be located proximate a perimeter of the baseplate 220. The transmitter retainer ring 224B may also be circular and may also be located proximate a perimeter of the transmitter unit 106. Other devices and configurations of the base retainer ring 224A and the transmitter retainer ring 224B may be employed to mechanically couple the transmitter unit 106 and the base unit 108 together. The configuration of the base retainer ring 224A and the transmitter retainer ring 224B may also provide for decoupling of the transmitter unit 106 and the base unit 108 from each other. For example, the base unit 108 may be separated from the transmitter unit 106 and a new base unit may be coupled to the existing transmitter unit as described herein.

The base retainer ring 224A may include a plurality of openings 226A configured to receive a plurality of tabs 226B located on the transmitter retainer ring 224B. In some embodiments, the tabs 226B may be located on the base retainer ring 224A and the openings 226A may be located on the transmitter retainer ring 224B. In some embodiments, the baseplate 220, the transmitter unit 106, the base retainer ring 224A, and/or the transmitter retainer ring 224B may be flexible (e.g., deformable) to enable the tabs 226B to be received in and withdrawn from the openings 226A. For example, the tabs 226B may be received in the openings 226A by forcing the transmitter unit 106 and the base unit 108 together. In some embodiments, the tabs 226B may be withdrawn from the openings 126B by bending one or both of the transmitter unit 106 or the base unit 108.

The base unit 108 may include a tube 228 extending from the baseplate 220. The tube 228 may have an opening 228A that passes through the baseplate 220 as described herein. The opening 228A may be configured to receive and enable operation of an inserter (e.g., inserter assembly 209—FIG. 2C) that implants the biosensor 110 (FIG. 1) subcutaneously. A portion of the biosensor 110 may pass through the side of the tube 228 so as to extend from the bottom of the baseplate 220. The tube 228 may be configured to be received within an opening 230 in the transmitter unit 106 when the transmitter unit 106 and the base unit 108 are mechanically coupled together so as to form a single passageway through the wearable device 102. Thus, the inserter may be operated from the top of the wearable device 102 via the opening 230 and the opening 228A. The tube 228 may include a rim 228B that may secure the base unit 108 to the transmitter unit 106 as described herein.

The transmitter unit 106 may include one or more transmitter contacts 244A (a few labelled) configured to electrically contact base contacts 244B (a few labelled) in the base unit 108. The base contacts 244B may at least partially encircle the tube 228. The transmitter contacts 244A may be mechanically biased toward the base unit 108 so that the transmitter contacts 244A contact the base contacts 244B in response to the base unit 108 and the transmitter unit 106 being coupled together. In some embodiments, the transmitter contacts 244A may be spring-loaded so as to mechanically bias the transmitter contacts 244A toward the base unit 108.

The transmitter unit 106 may include transmitter circuitry (e.g., transmitter circuitry 456, FIG. 4A) encased or otherwise located in a structure 258, such as a molded structure or other structure. In some embodiments, the structure 258 may be an overmold of the transmitter circuitry 456. Example transmitter circuitry 456 may include an analog front end configured to electrically bias conductors and the like electrically coupled to the biosensor 110 (FIG. 1) and to sense current passing through the biosensor 110. The transmitter circuitry 456 may include operational amplifiers, current sources, current sensing circuitry, comparators, etc. Other transmitter circuitry 456 may include processing circuitry such as analog-to-digital converters for digitizing current signals, and memory for storing digitized current signals. The transmitter circuitry 456 may also include a controller such as a microprocessor, a microcontroller, or the like configured to compute analyte concentration levels based on measured current signals, and circuitry for transmitting analyte concentration levels to the external device 104 (FIG. 1).

The transmitter unit 106 may also include a recess 260 configured to partially receive the battery 234. The recess 260 may be formed in a portion of the structure 258, for example. In other embodiments, the recess 260 may be formed from another structure (not shown). The recess 260 may hold the battery 234 in a predetermined location when the transmitter unit 106 and the base unit 108 are coupled together. The recess 260 may include a rim 260A that at least partially surrounds the recess 260. The rim 260A contacts a side portion of the battery 234 when the transmitter unit 106 and the base unit 108 are coupled together to maintain the battery 234 in the fixed location.

The base unit 108 may include the battery 234 or other power source or may be configured to receive the battery 234 or other power source. The battery 234 or other power source may supply power to both the base unit 108 and the transmitter unit 106 when the base unit 108 and the transmitter unit 106 are coupled together. The base unit 108 is described herein as having the battery 234 received therein, however, the base unit 108 may have other power sources received therein. In some embodiments, the battery 234 is the sole source of power for the wearable device 102.

Additional reference is made to FIG. 2D, which is a top isometric view of an embodiment of the battery 234. The battery 234 may include a conductive case, which may be the cathode terminal 234C. A center portion of the top of the battery 234 includes the anode terminal 234A. The cathode terminal 234C and the anode terminal 234A are separated by an insulator 234I. The battery 234 shown in FIG. 2B is oriented with the anode terminal 234A facing the baseplate 220 and is out of view. In other embodiments, the anode terminal 234A may face away from the baseplate 120 and may contact a component on the transmitter unit 106 as described herein. Examples of the battery 234 include flexible lithium polymer batteries, coin cell batteries such as lithium manganese, silver oxide, and alkaline coin batteries (e.g., CR 2032, SR516, and LR60 type coin batteries), or the like. Other power sources and/or battery types may be used.

As described herein, the base unit 108 may be sterilized with the battery 234 located therein, so the battery 234 may be configured to withstand (e.g., remain operational) when the base unit 108 is sterilized. In some embodiments, the base unit 108 is sterilized using electron beam sterilization (e.g., E-beam radiation or sterilization), so the battery 234 may be configured to remain functional after exposure to the E-beam radiation. In some embodiments, the electron beam sterilization level is up to 25 KGy. Other radiation levels may be used and the battery 234 may be configured to withstand these other radiation levels. As also described herein, the base unit 108 may have components applied (e.g., molded) thereto, so the battery 234 may be configured to withstand a molding environment. In some embodiments, the molding may expose the battery 234 to a temperature of up to 90° C. for one minute. Accordingly, the battery 134 may be configured to withstand a temperature of 90° C. for one minute. The molding may subject the battery 234 to other temperatures for other time periods. Accordingly, the battery 234 may be configured to withstand the other temperatures and time periods.

In the embodiment of FIG. 2B, the base unit 108 may include a cup 238 that retains the battery 234 in the base unit 108. The cup 238 may be affixed to the baseplate 220. In some embodiments, the cup 238 may be formed by an overmold process performed after formation of the baseplate 220, for example. In other embodiments, the cup 238 may be a component that is attached to the baseplate 220 as described herein. The cup 238 may include a rim 238A that may secure the battery 234 and/or maintain the battery 234 in a fixed location. In some embodiments, the rim 238A may encircle the cup 238. In other embodiments, the rim 238A may partially encircle the cup 238.

The wearable device 102 illustrated in FIG. 2C shows an inserter assembly 209 configured to engage the wearable device. For example, the inserter assembly 209 may include a trocar 209A that is configured to be received in the opening 230 to locate the biosensor 110 (FIG. 1) subcutaneously.

Figure 3A:
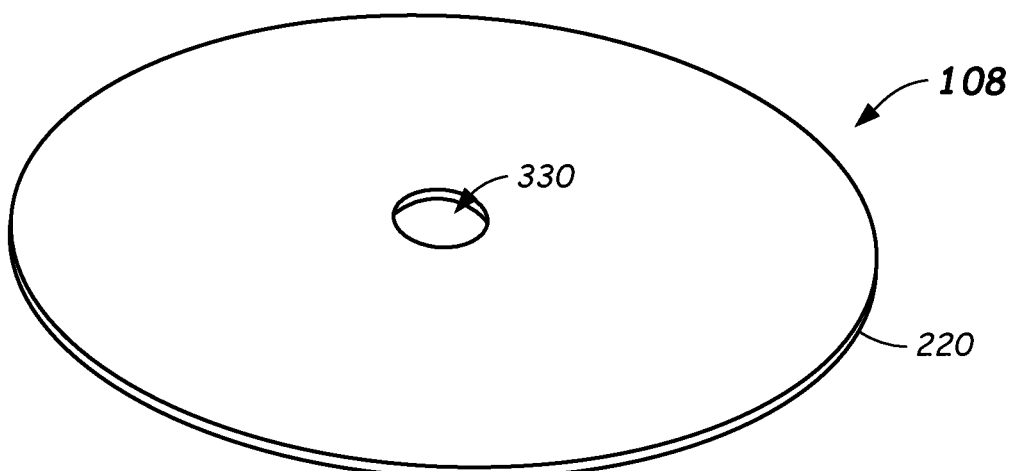
FIGS. 3A-3F illustrate top isometric views of various stages of a method of manufacturing of a base unit of a wearable device of a continuous analyte monitoring system in accordance with one or more embodiments.

Additional reference is made to FIGS. 3A-3F, which illustrate various stages of the base unit 108 (FIG. 2B) during a process of manufacturing an embodiment of the base unit 108. The process commences with forming the baseplate 220 as shown in FIG. 3A, which is an isometric view of the baseplate 220. The baseplate 220 may have a hole 330 extending there through. The hole 330 may be aligned with the opening 228A (FIG. 3B) in the tube 228 when the base unit 108 (FIG. 2B) and the transmitter unit 106 (FIG. 2A) are coupled together. Accordingly, the hole 330 may be sized to receive an insertion tool (not shown) that inserts the biosensor 110 (FIG. 1) subcutaneously. In some embodiments, the baseplate 220 may be disc-shaped. In some embodiments, the baseplate 220 may be formed from a plastic, such as, but not limited to, acrylonitrile butadiene styrene (ABS), polycarbonate, nylon, acetal, polyphthalamide (PPA), polysulfone, polyethersulfone, polyetheretherketone (PEEK), polypropylene, high-density polyethylene (HDPE), and low-density polyethelene (LDPE). Other suitable materials may be used in the baseplate 220.

Figure 3B:
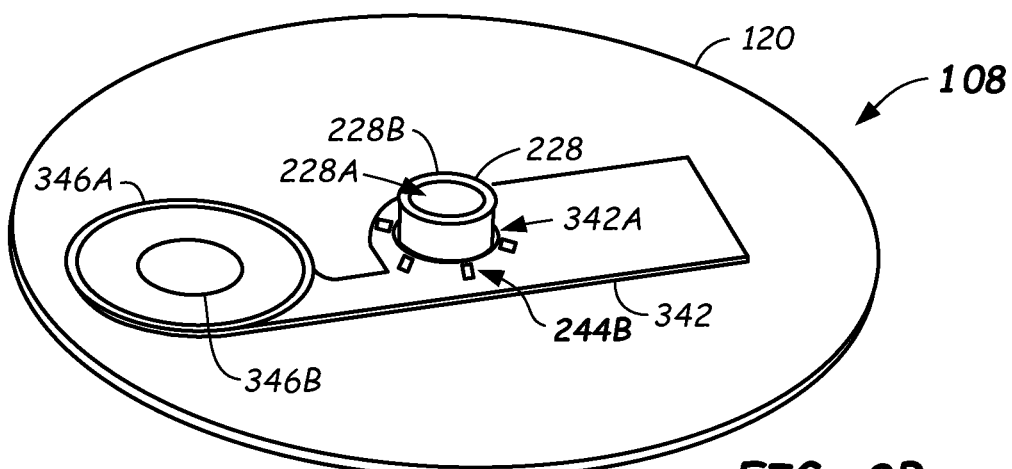

Additional reference is made to FIG. 3B, which illustrates an isometric view of the baseplate 220 with a substrate 342 and the tube 228 attached thereto. In some embodiments, the substrate 342 may be a printed circuit board and may have electrical traces (not shown) located therein. As shown in FIG. 3B, the substrate 342 may include a hole 342A that is configured to receive the tube 228. In some embodiments, the substrate 342 may not include the hole 342A, but may have a shape that at least partially receives or accommodates the tube 228. In some embodiments, the substrate 342 may be flexible so as to flex with the baseplate 220. The flexibility may prevent the substrate 342 from being damaged as the base unit 108 is flexed to couple to and decouple from the transmitter unit 106.

The substrate 342 may include the one or more base contacts 244B configured to electrically contact the transmitter contacts 244A (FIG. 2A) located in the transmitter unit 106. As described in greater detail below, the base contacts 244B may conduct current between the battery 234 and the transmitter unit 106 (FIG. 2A) by way of the electrical contact between the base contacts 244B and the transmitter contacts 244A. In the configuration of the substrate 342 shown in FIGS. 3B-3E, the substrate 342 may include a first battery contact 346A (e.g., a first power source contact) and a second battery contact 346B (e.g., a second power source contact) that are configured to electrically contact terminals of the battery 234 (FIG. 2D). For example, the first battery contact 346A may be configured to electrically contact the cathode terminal 234C (FIG. 2D) of the battery 234 and the second battery contact 346B may be configured to electrically contact the anode terminal 234A (FIG. 2D) of the battery 234. The heights of the first battery contact 346A and the second battery contact 346B may be different to accommodate different heights of the cathode terminal 234C and the anode terminal 234A. Other configurations of contacts between the terminals of the battery 234 and contacts within the wearable device 102 (FIG. 2C) are described herein. The coupling of the base unit 108 and the transmitter unit 106 may provide a force on the battery 234 that forces the battery 234 to at least one of the first battery contact 346A or the second battery contact 346B.

Figure 3C:
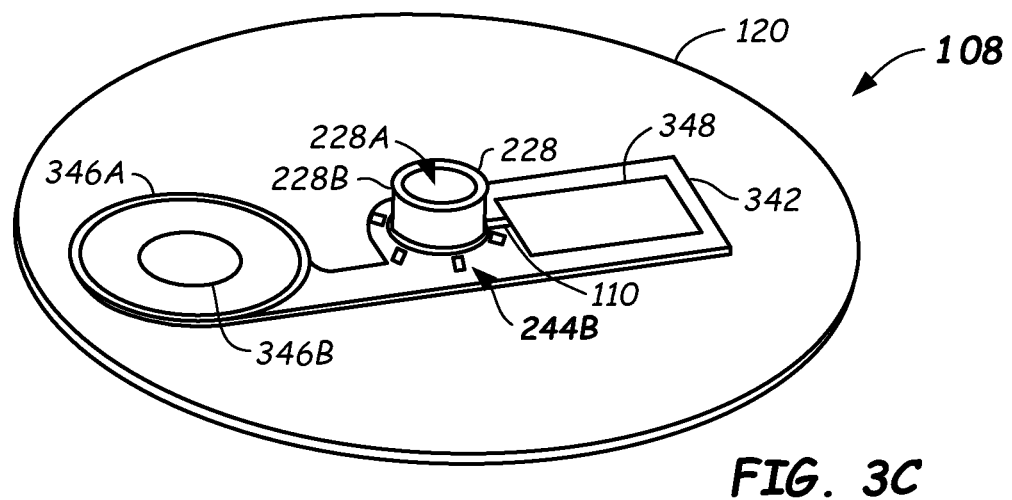

Additional reference is made to FIG. 3C, which illustrates base circuitry 348 coupled to the substrate 342. The portion of the base unit 108 shown in FIG. 3C may contain electrical connectors and the like that electrically couple the portion of the base unit 108 configured to be subcutaneously implanted to the base circuitry 348. In some embodiments, the base circuitry 348 is electrically coupled to traces (not shown) or the like that electrically couple to the base contacts 244B. In some embodiments, other components (not shown) may be electrically and mechanically coupled to the base circuitry 348 and electrically coupled to the base contacts 244B.

Figure 3D:
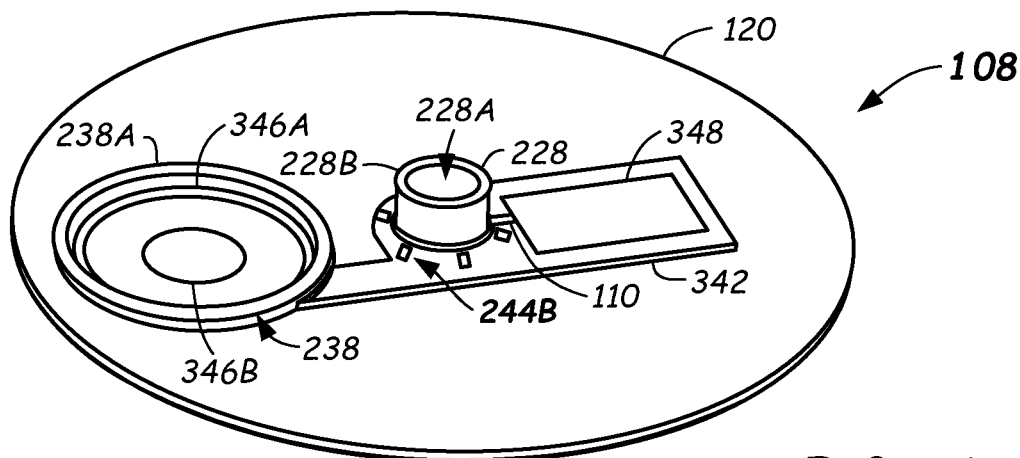
Figure 3E:
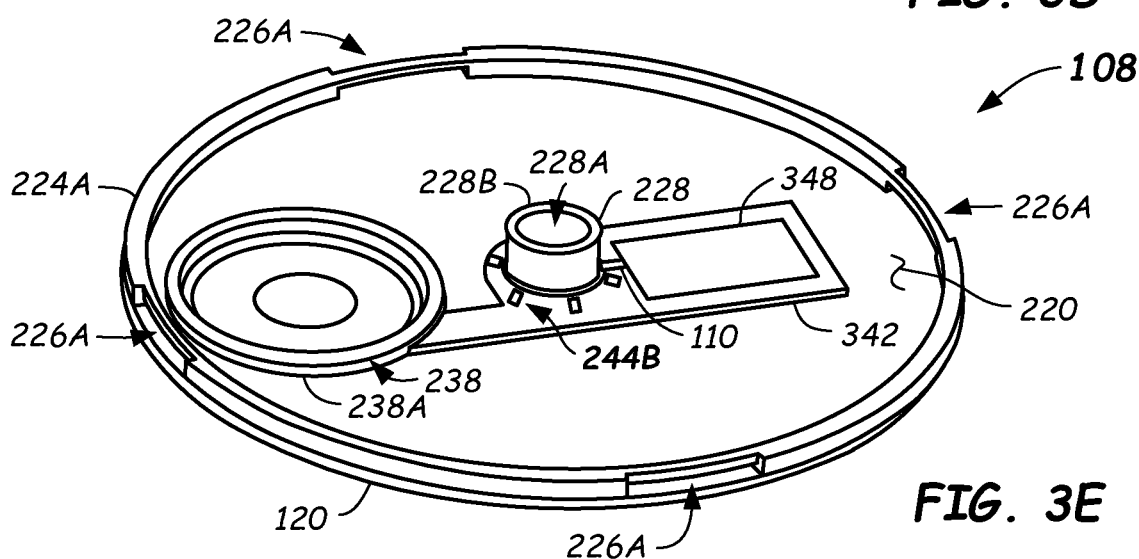
Figure 3F:
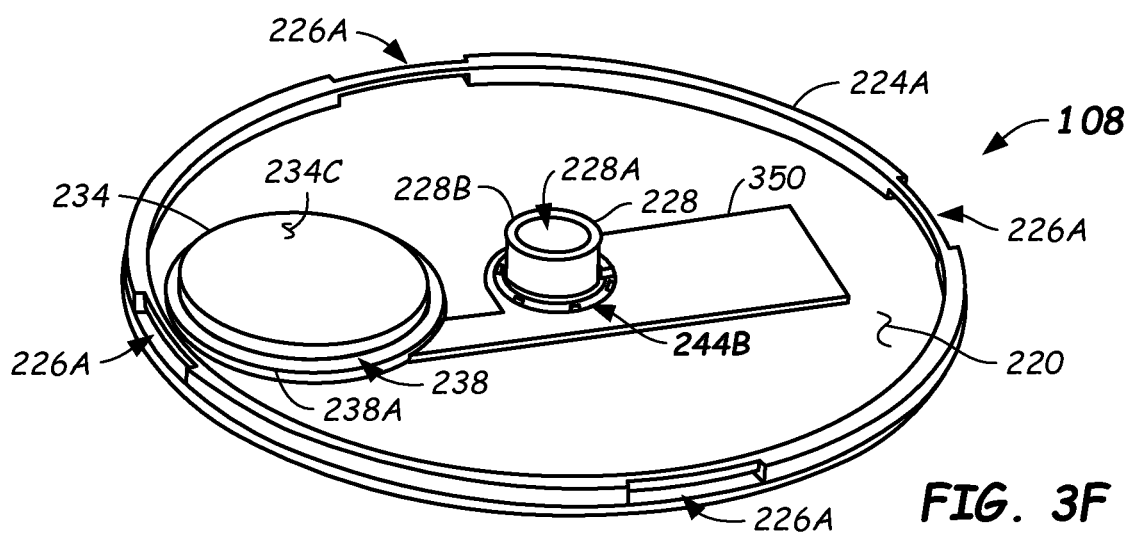

Additional reference is made to FIG. 3D, which shows the base unit 108 with the cup 238 attached to the substrate 342. In some embodiments, the cup 238 may also be at least partially attached to the baseplate 220. In the embodiment of FIGS. 3D-3F, the cup 238 is configured to encircle the battery 234 when the battery 234 is received in the cup 238. In some embodiments, the cup 238 may be formed by a molding process. In other embodiments, the cup 238 may be formed separate from the base unit 108 and attached to the substrate 342 and/or the baseplate 220. In some embodiments, the cup 238 may be flexible or made of a flexible material and may be slightly smaller than the diameter of the battery 234, so that the battery 234 fits snuggly within the cup 238. For example, friction between the battery 234 and the rim 238A may retain the battery 234 within the cup 238. In other embodiments, the rim 238A and/or the cup 238 may partially encircle the battery 234.

Additional reference is made to FIG. 3E, which shows the base unit 108 with the base retainer ring 224A attached thereto. In some embodiments, the base retainer ring 224A may be attached to the baseplate 220. In some embodiments, the base retainer ring 224A may be made of the same material as the baseplate 220 and the baseplate 220 may remain flexible even with the attachment of the base retainer ring 224A. In some embodiments, the base retainer ring 224A may be molded to the base unit 108, such as molded to the baseplate 220. In other embodiments, the base retainer ring 224A may be fabricated separate from the other components of the base unit 108 and attached using and adhesive, for example.

Additional reference is made to FIG. 3F, which shows an embodiment of the finished base unit 108. In the embodiment of FIG. 3F, a portion of the substrate 342 has been covered by a coating 350. In some embodiments, the coating 350 may be a conformal coating or a mold compound. Other coating materials and processes may be used. The coating 350 may provide a liquid seal over the substrate 342 to protect the substrate 342, the base circuitry 348, and other components thereon from exposure to contaminants. In the embodiment of FIG. 3F, the base contacts 244B are not covered by the coating 350 so that the base contacts 244B may electrically contact the transmitter contacts 244A (FIG. 2A) in response to the base unit 108 and the transmitter unit 106 being coupled together.

The completed base unit 108 may be packaged for market and then sterilized. For example, the base unit 108 may be packaged in a sealed package that ultimately may be sent to a user of the base unit 108. In some embodiments, the package may be hermetically sealed. Other methods of sealing the package may prevent contaminants, including biological material, from contacting the base unit 108. Sterilization may include exposing the base unit 108, while in the package, to radiation, such as e-beam sterilization. As described herein, the battery 234 may be rad-hard, so it is not damaged and remains functional when exposed to the radiation. In some embodiments, gamma ray, E-beam sterilization, or another sterilization method may be employed to sterilize the base unit 108. In some embodiments, the E-beam sterilization is applied at a level of 25 KGy and the battery 234 is configured to withstand this radiation.

Reference is made to FIGS. 2A-2C to describe coupling the transmitter unit 106 and the base unit 108 together. In the embodiment of FIG. 2B, the base unit 108 is complete and includes the battery 234 or other power source that provides power to both the transmitter unit 106 and the base unit 108. The transmitter unit 106 and the base unit 108 may have orientation features that only enable coupling of the transmitter unit 106 and the base unit 108 when the transmitter unit 106 and the base unit 108 are properly aligned. In some embodiments, the openings 226A and the tabs 226B are not evenly spaced, so the tabs 226B will only engage the openings 226A when the transmitter unit 106 and the base unit 108 are properly aligned. Other alignment devices may be used.

A user may mechanically couple the transmitter unit 106 and the base unit 108 together as described herein. For example, a user may press the transmitter unit 106 and the base unit 108 together, which forces the tabs 226B of the transmitter retainer ring 224B into the openings 226A of the base retainer ring 224A. In addition to the foregoing coupling, the rim 228B of the tube 228 may engage with the opening 230. In some embodiments, the engagement of the opening 230 with the rim 228B may further secure and/or couple the transmitter unit 106 and the base unit 108 together. In some embodiments, the engagement of the rim 228B with the opening 230 may enhance the rigidity of the wearable device 102. For example, the tube 228 may prevent the wearable device 102 from crushing. During the coupling, the battery 234 (or other power source) may be received in the recess 260 and may abut against the rim 260A to maintain the battery 234 in a fixed location.

Figure 4A:
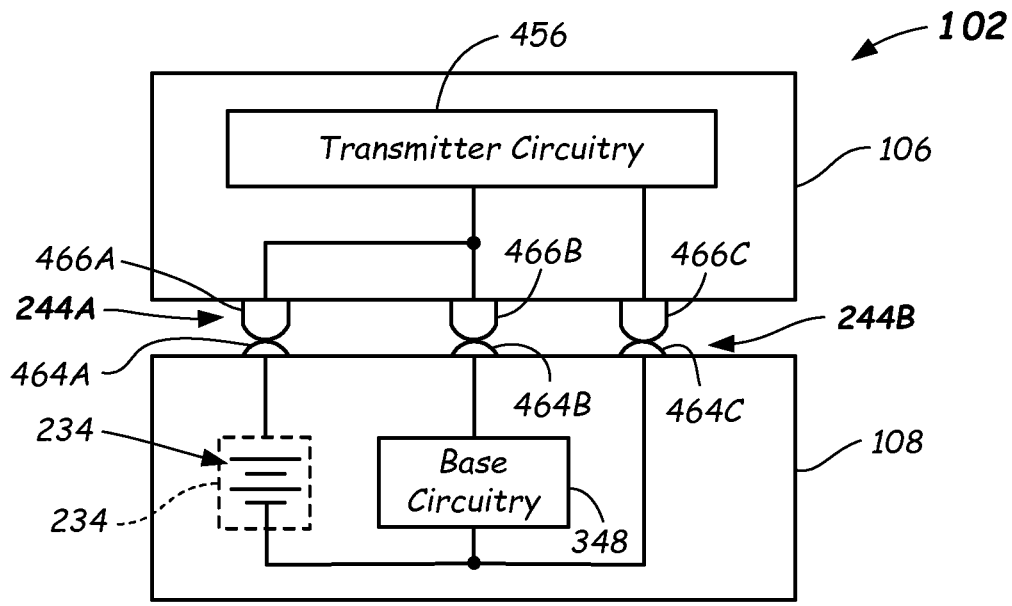
FIG. 4A illustrates a schematic diagram showing power circuitry between a battery, a transmitter unit, and a base unit of a wearable device of a continuous analyte monitoring system according to one or more embodiments.

In response to the mechanical coupling of the transmitter unit 106 and the base unit 108, the battery 234 may provide power to the transmitter unit 106 and the base unit 108. Reference is made to FIG. 4A, which is a schematic diagram showing an embodiment of power circuitry between the battery 234, the transmitter unit 106, and the base unit 108. In the embodiment of FIG. 4A, the transmitter contacts 244A have electrically contacted the base contacts 244B in response to the transmitter unit 106 and the base unit 108 being coupled together. As described above, the transmitter contacts 244A may be mechanically biased toward the base unit 108 or the base contacts 244B when the transmitter unit 106 and the base unit 108 are coupled together to improve or make electrical coupling between the transmitter contacts 244A and the base contacts 244B. In other embodiments, the base contacts 244B may be biased toward the transmitter contacts 244A.

As described herein, the battery 234 may conduct power to the transmitter unit 106 and the base unit 108 in response to the coupling of the transmitter unit 106 and the base unit 108. A first base contact 464A may be electrically coupled to the cathode terminal 234C of the battery 234 and may be electrically coupled to a first transmitter contact 466A. The first transmitter contact 466A may be electrically coupled to a second transmitter contact 466B by a conductor within the transmitter unit 106. The second transmitter contact 466B may be electrically coupled to the transmitter circuitry 456 and a second base contact 464B, which may be electrically coupled to the base circuitry 348 in the base unit 108.

The anode of the battery 234 is coupled to the base circuitry 348 and a third base contact 464C, which contacts a third transmitter contact 466C. The third transmitter contact 466C is electrically coupled to the transmitter circuitry 456. As shown in FIG. 4A, both the transmitter circuitry 456 and the base circuitry 348 receive power in response to the coupling of the transmitter unit 106 and the base unit 108. In some embodiments, the transmitter unit 106 and the base unit 108 may include other contacts that conduct data and/or electrical signals between the transmitter unit 106 and the base unit 108. In addition to the foregoing, the battery 234 is not electrically connected to any components unless the transmitter unit 106 and the base unit 108 are coupled together, which prevents drainage of the battery 234.

Figure 4B:
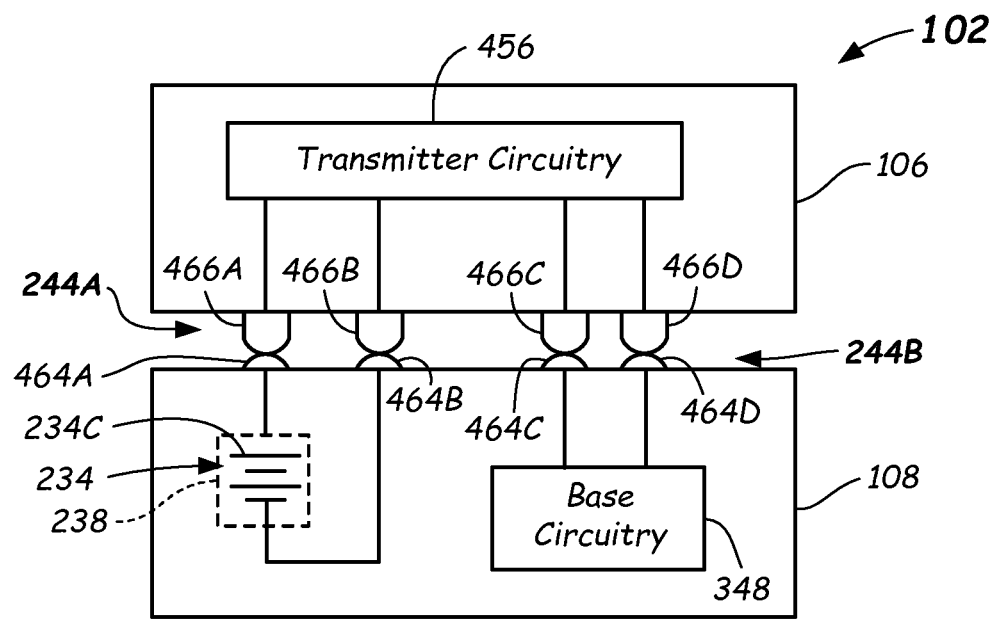
FIG. 4B illustrates a schematic diagram showing another embodiment of power circuitry between a battery, a transmitter unit, and a base unit of a wearable device of a continuous analyte monitoring system according to one or more embodiments.

Reference is now made to FIG. 4B, which is a schematic diagram showing another embodiment of power circuitry within the wearable device 102. In the embodiment of FIG. 4B, the cathode terminal 234C of the battery 234 is electrically coupled to the first base contact 464A and the anode terminal 234A of the battery 234 is electrically coupled to the second base contact 464B. The first base contact 464A contacts the first transmitter contact 466A and the second base contact 464B contacts the second transmitter contact 466B in response to coupling of the transmitter unit 106 and the base unit 108. As shown in FIG. 4B, the first transmitter contact 466A and the second transmitter contact 466B are electrically coupled to the transmitter circuitry 456 and, thus, provide power from the battery 234 to the transmitter circuitry 456 in response to the coupling of the transmitter unit 106 and the base unit 108.

The third transmitter contact 466C contacts the third base contact 464C and a fourth transmitter contact 466D contacts a fourth base contact 464D in response to the coupling of the transmitter unit 106 and the base unit 108 together. These contacts electrically couple the transmitter circuitry 456 with the base circuitry 348. Thus, electric signals and/or voltages may be transmitted between the transmitter circuitry 456 and the base circuitry 348 in response to coupling of the transmitter unit 106 and the base unit 108 together. In addition, the battery 234 is not electrically coupled to any components unless the transmitter unit 106 and the base unit 108 are coupled together, which prevents drainage of the battery 234.

Figure 5A:
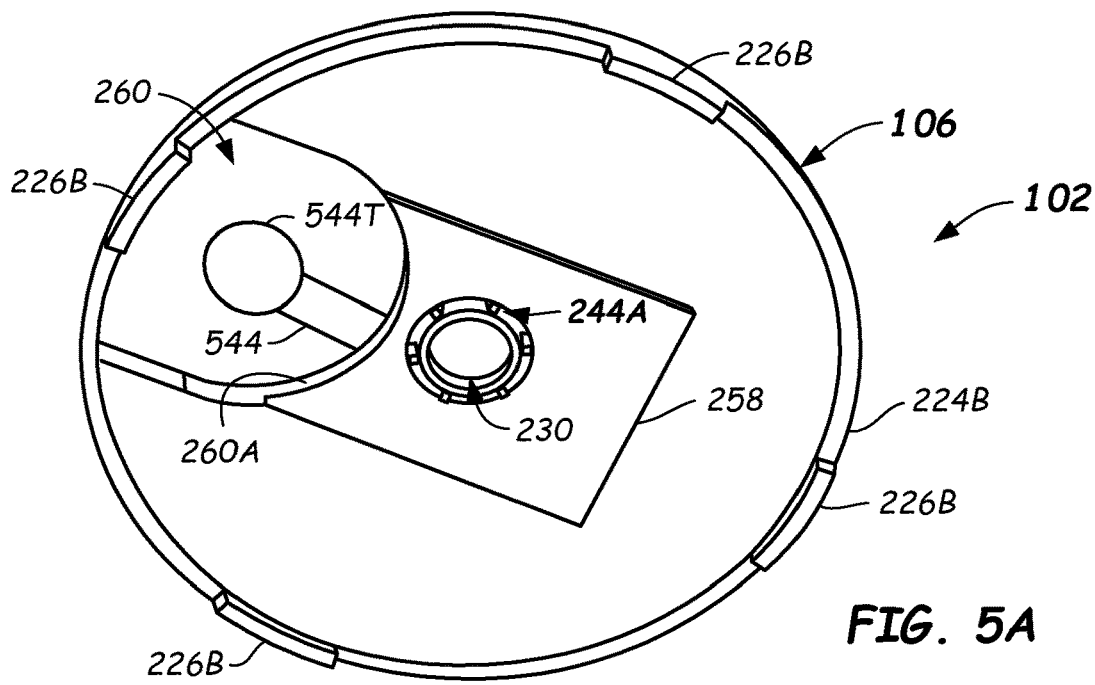
FIG. 5A illustrates a bottom isometric view of a transmitter unit of a wearable device of a continuous analyte monitoring system including a contact configured to electrically contact a terminal of a battery according to one or more embodiments.

Reference is now made to FIGS. 5A-5D, which illustrate embodiments of the transmitter unit 106 and the base unit 108, wherein one terminal of the battery 234 is configured to directly electrically contact a contact in the transmitter unit 106 in response to the transmitter unit 106 and the base unit 108 being coupled together. Referring to FIG. 5A, the transmitter unit 106 may include a transmitter contact 544T that electrically contacts a terminal of the battery 234 (FIG. 5B) in response to the transmitter unit 106 and the base unit 108 being coupled together. In the embodiment of FIG. 5A, the transmitter contact 544T is located in the recess 260 that is configured to retain the battery 234 in response to the transmitter unit 106 and the base unit 108 being coupled together. In some embodiments, the transmitter contact 544T is a dome pad or the like extending from a circuit board 544 or the like. In some embodiments, the transmitter contact 544T is biased toward the base unit 108 by a spring or similar device (not shown) that provides a sturdy electrical connection between the transmitter contact 544T and the battery 234 in response to the transmitter unit 106 and the base unit 108 being coupled together.

Figure 5B:
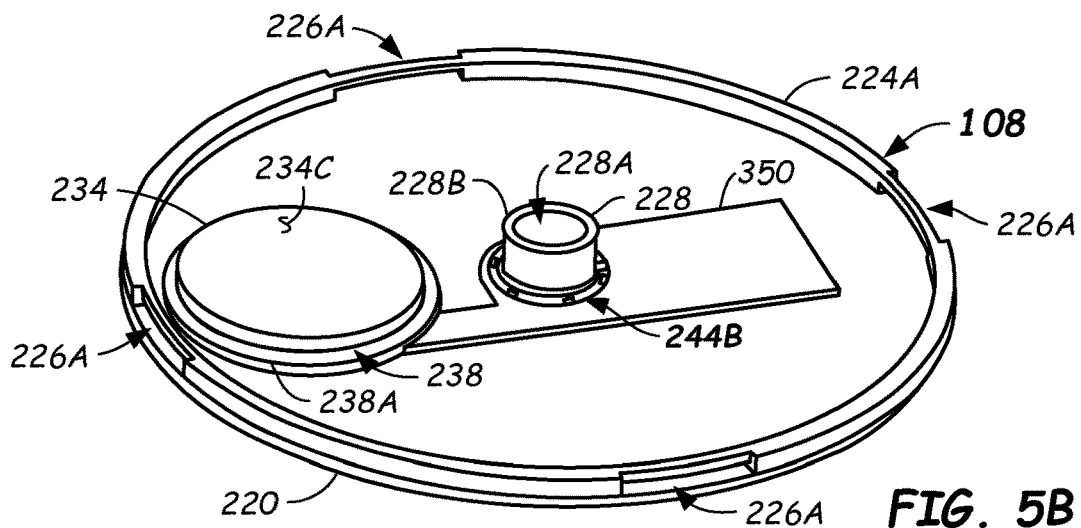
FIG. 5B illustrates a top isometric view of a base unit of a wearable device of a continuous analyte monitoring system including a battery configured to electrically contact a contact in the transmitter unit of FIG. 5A according to one or more embodiments.

The embodiment of the base unit 108 shown in FIG. 5B includes the battery 234 received in the cup 238. In the embodiment of FIG. 5B, the cathode terminal 234C of the battery 234 faces the transmitter unit 106 and is configured to contact the transmitter contact 544T in response to the transmitter unit 106 and the base unit 108 being coupled together. In other embodiments, the wearable device 102 may be configured so that the anode terminal 234A of the battery 234 contacts the transmitter contact 544T in response to the transmitter unit 106 and the base unit 108 being coupled together.

Figure 5C:
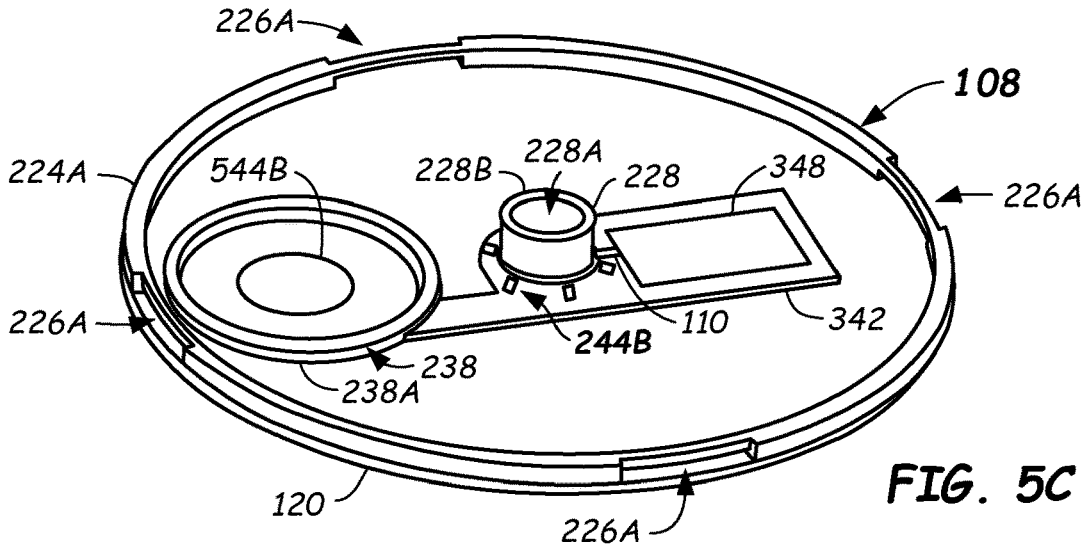
FIG. 5C illustrates the base unit of FIG. 5B with the battery removed according to one or more embodiments.

FIG. 5C illustrates an embodiment of the base unit 108 with the battery removed. As shown in FIG. 5C, the cup 238 may include a base contact 544B that is configured to contact the anode terminal 234A (FIG. 2D) or the cathode terminal 234C of the battery 234 in response to the battery 234 being received in the cup 238 as shown in FIG. 5B. In some embodiments, the cup 238 may include only a single base contact 544B.

Figure 5D:
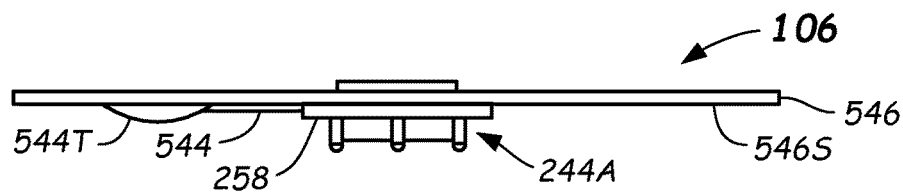
FIG. 5D illustrates a side elevation view of an embodiment of the transmitter unit of FIG. 5A according to one or more embodiments.

FIG. 5D illustrates a side elevation view of the transmitter unit 106 with the transmitter retainer ring 224B (FIG. 5A) removed. The transmitter unit 106 may include a plate 546, which may be a substrate. The plate 546 has a surface 546S which may face the base unit 108 when the transmitter unit 106 and the base unit 108 are coupled together. The view of FIG. 5D shows the transmitter contact 544T being at least partially dome-shaped and extending from the surface 546S of the plate 546. The dome shape of the transmitter contact 544T enables the transmitter contact 544T to contact the battery 234 or other contact in the base unit 108. As shown, the circuit board 544 is configured to conduct current between the battery 234 and the transmitter circuitry.

Figure 6:
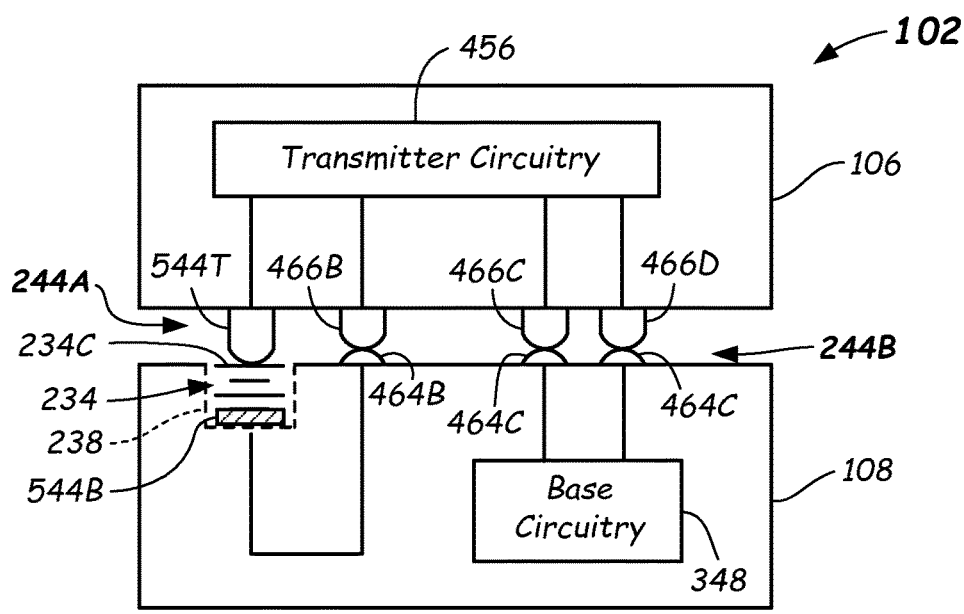
FIG. 6 illustrates a schematic diagram of an embodiment of circuitry of a transmitter unit and a base unit of a wearable device of a continuous analyte monitoring system according to one or more embodiments.

Additional reference is made to FIG. 6, which schematically illustrates an embodiment of circuitry of the wearable device shown in FIGS. 5A-5D. In the schematic diagram of FIG. 6, the base unit 108 and the transmitter unit 106 are coupled together. As shown in FIG. 6, the transmitter contact 544T electrically contacts the cathode terminal 234C of the battery 234. The embodiments of FIGS. 5A-6 illustrate using one of the terminals of the battery 234 as a contact of the base unit 108, which reduces the number of remaining contacts in the base unit 108. In addition, the embodiments of FIGS. 5A-6 do not permit any leakage from the battery 234 until the transmitter unit 106 and the base unit 108 are coupled together, which completes a circuit between the battery 234 and the transmitter unit 106.

Figure 7:
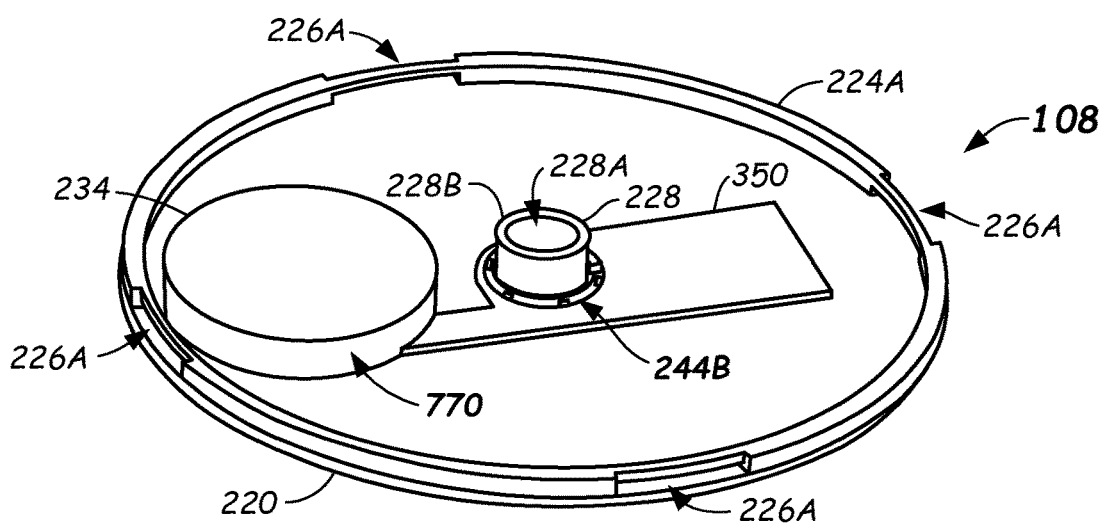
FIG. 7 illustrates a base unit of a wearable device of a continuous analyte monitoring system including a battery overmolded or otherwise encapsulated in a mold according to one or more embodiments.

Additional reference is now made to FIG. 7, which illustrates an embodiment of the base unit 108 with the battery (not shown in FIG. 7) overmolded or otherwise encased in a mold 770 (e.g., an encapsulant). In some embodiments, the mold 770 may be applied to the configuration of the base unit 108 shown in FIG. 3F wherein a portion of the battery 234 is exposed. In some embodiments, the entire baseplate 220, except for the base contacts 244B, is covered by the mold 770. In other embodiments, the mold 770 may cover just the battery 234 (FIG. 3F) and/or locations proximate the battery 234. For example, the mold 770 may cover the rim 238A. In some embodiments, the mold 770 may secure the battery 234 into a specific location, such as the cup 238 (FIG. 2B), in the baseplate 220.

In some embodiments, the mold 770 may be formed from a single layer or multiple layers. For example, the mold 770 may be formed from one or more layers of liquid silicone rubber (LSR), a thermoplastic elastomer (TPE), or the like. Other materials may be used such as, but not limited to, ABS, polycarbonate, nylon, acetal, PPA, polysulfone, polyethersulfone, PEEK, polypropylene, HDPE, LDPE, etc. Other materials may be used. In some embodiments, the mold 770 may be formed at a temperature of greater than 100° C. and in some embodiments the mold 770 may be formed at a temperature of greater than 80° C. The battery 234 may be configured to withstand the temperatures of the mold 770.

Figure 8A:
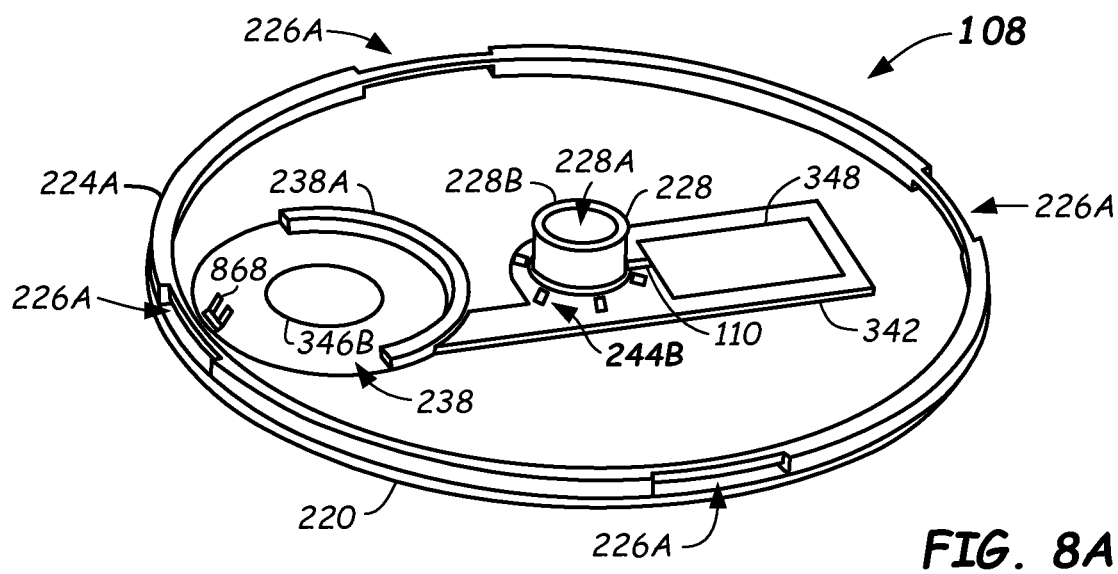
FIG. 8A illustrates top isometric view of a base unit of a wearable device of a continuous analyte monitoring system including a spring conductor configured to electrically contact a terminal of a battery and to retain the battery in the base unit according to one or more embodiments.
Figure 8B:
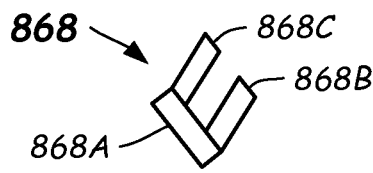
FIG. 8B illustrates an enlarged top isometric view of an embodiment of the spring conductor of FIG. 8A according to one or more embodiments.

Reference is made to FIG. 8A, which illustrates an embodiment of the base unit 108 with a spring contact 868 configured to force the battery 234 (FIG. 2D) against the rim 238A of the cup 238. FIG. 8B illustrates an enlarged view of an embodiment the spring contact 868 of FIG. 8A. The spring contact 868 may be made of a conductive material and flexible material, such as steel, that forces the battery 234 to the rim 238A of the cup 238. The spring contact 868 may include a base portion 868A that may be affixed to a structure within the base unit 108 that conducts current from the battery 234. The spring contact 868 may include one or more spring members that extend from the base portion 868A and flex relative to the base portion 868A so as to force the battery 234 to the rim 238A of the cup 238. In the embodiment of FIGS. 8A and 8B, the spring contact 868 has a first spring member 868B and a second spring member 868C attached to the base portion 868A. In use, the battery 234 is positioned into the cup 238. The anode terminal 234A electrically contacts with the second battery contact 346B and the cathode terminal 234C electrically contacts with the spring contact 868. The spring contact 868 conducts current similar to the first battery contact 346A (FIG. 3B) and/or the second battery contact 346B (FIG. 3B). The battery 234 and/or other components of the base unit 108 may be overmolded to retain the battery 234 within the cup 238.

Figure 9:
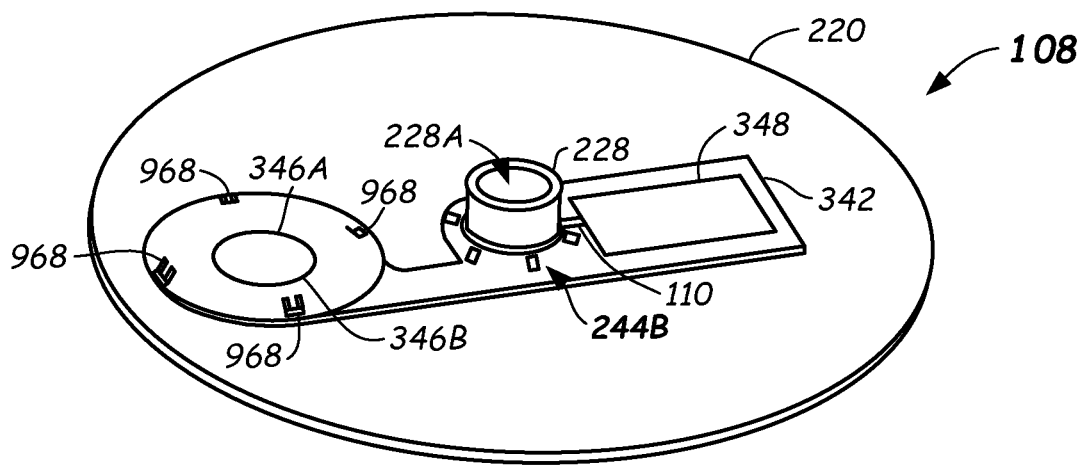
FIG. 9 illustrates top isometric view of a base unit of a wearable device of a continuous analyte monitoring system including a plurality of spring conductors configured to electrically contact a terminal of a battery and to retain the battery in the base unit according to one or more embodiments.

Additional reference is made to FIG. 9, which illustrates an embodiment of the base unit 108 including a plurality of spring contacts 968 configured to contact at least one of the terminals of the battery 234 (FIG. 2D). In some embodiments, one or more of the spring contacts 968 may be identical or substantially similar to the spring contact 868 (FIG. 8B). In the embodiment of FIG. 9, the base unit 108 includes four spring contacts 968. In other embodiments, the base unit 108 may include different numbers of spring contacts 968. The spring contacts 968 may mechanically and electrically contact the cathode terminal 234C (FIG. 2D) of the battery 234. For example, the spring contacts 968 may contact the perimeter 234P of the battery 234, wherein friction between the spring contacts 968 and the perimeter 234P retains the battery 234 in a fixed location in the base unit 108. Accordingly, the plurality of spring contacts 968 may form a cup that retains the battery 234. The fixed location maintains electrical contact between the anode terminal 234A of the battery 234 and the first battery contact 346A, which completes a circuit with the battery 234. The recess 260 (FIG. 5A) in the transmitter unit 106 may further retain the battery 234 in the fixed location.

Referring to FIGS. 2A-2C, both the transmitter unit 106 and the base unit 108 may be sealed units (e.g., waterproof), with only electrical contacts of the transmitter unit 106 and the base unit 108 exposed as described herein. Once the transmitter unit 106 and the base unit 108 are physically coupled together, the electrical contacts may also be sealed from the external environment, such as by the use of a sealing member (not shown).

Figure 10:
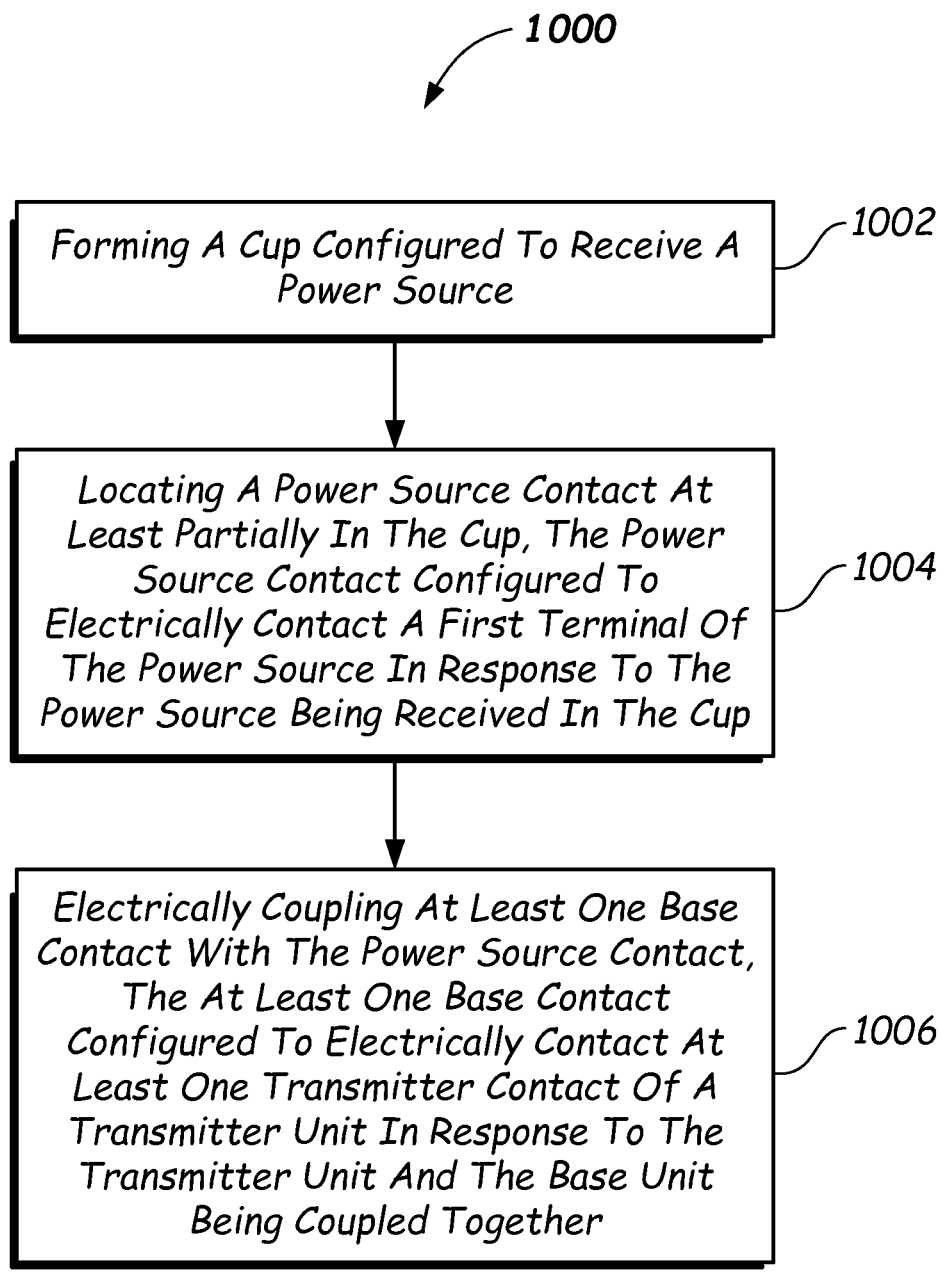
FIG. 10 is a flowchart showing of a method of manufacturing a base unit of a wearable device of a continuous analyte monitoring system according to one or more embodiments.

Reference is now made to FIG. 10, which illustrates a flowchart showing a method 1000 of manufacturing a base unit (e.g., base unit 108) of a wearable device (e.g., wearable device 102) of a continuous analyte monitoring system (e.g., continuous analyte monitoring system 100). The method 1000 includes, in 1002, forming a cup (e.g., cup 238) configured to receive a power source (e.g., battery 234). The method 1000 includes, in 1004, locating a power source contact (e.g., first battery contact 346A, second battery contact 346B) at least partially in the cup, the power source contact configured to electrically contact a first terminal (e.g., anode terminal 234A, cathode terminal 234C) of the power source in response to the power source being received in the cup. The method 1000 includes, in 1006, electrically coupling at least one base contact (e.g., base contacts 244B) with the first power source contact, the at least one base contact configured to electrically contact at least one transmitter contact (e.g., transmitter contacts 244A) of a transmitter unit (e.g., transmitter unit 106) in response to the transmitter unit and the base unit being coupled together.

Figure 11:
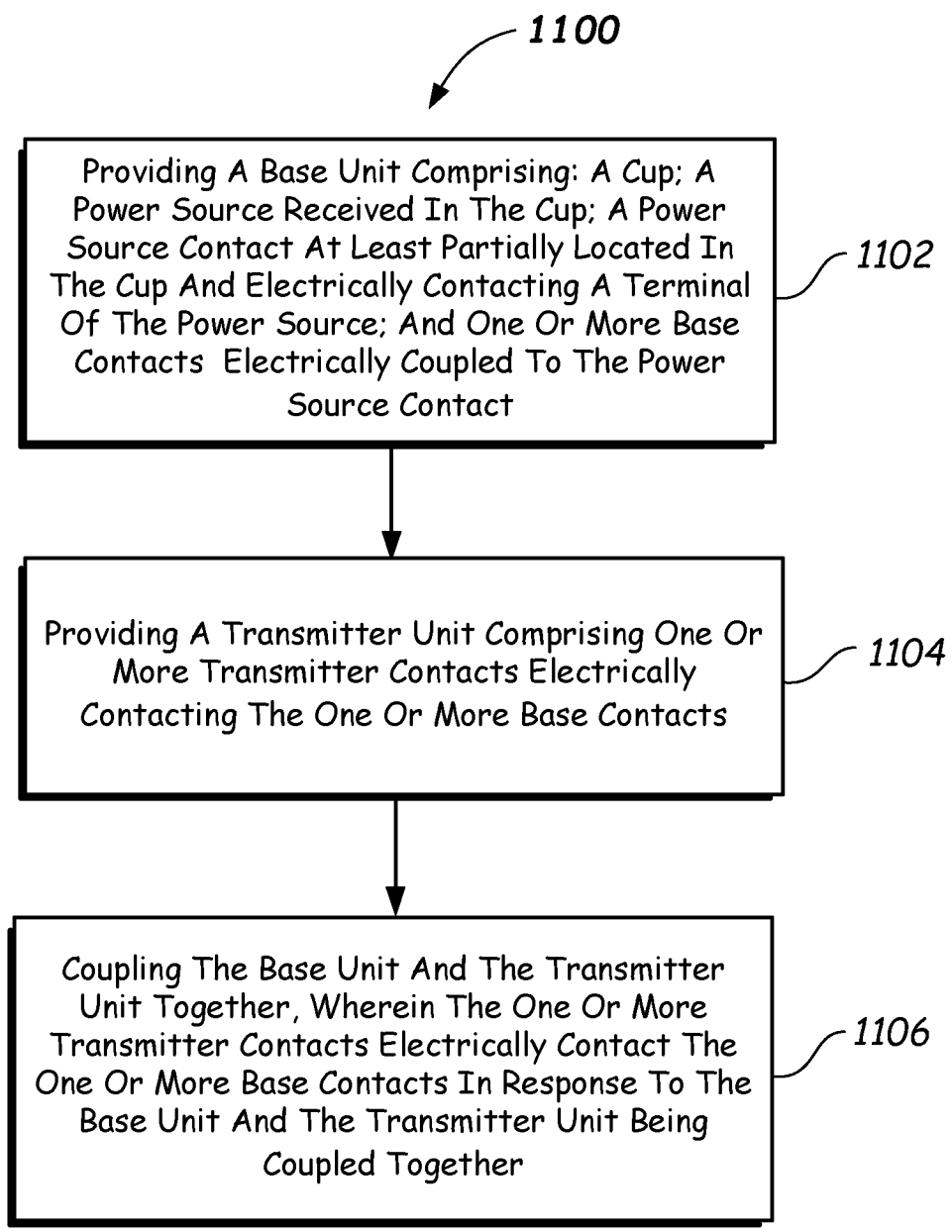
FIG. 11 is a flowchart showing of a method of using a wearable device a continuous analyte monitoring system according to one or more embodiments.

Reference is made to FIG. 11, which illustrates a flowchart showing a method 1100 of using a wearing device (e.g., wearable device 102) of a continuous analyte monitoring system (e.g., continuous analyte monitoring system 100). The method 1100 includes, in 1102, providing a base unit (e.g., base unit 108) comprising: a cup (e.g., cup 238); a power source (e.g., battery 234) received in the cup; a power source contact (e.g., first battery contact 346A, second battery contact 346B) at least partially located in the cup and electrically contacting a terminal (e.g., anode terminal 234A, cathode terminal 234C) of the power source; and one or more base contacts (e.g., base contacts 244B) electrically coupled to the power source contact. The method 1100 includes, in 1104, providing a transmitter unit (e.g., transmitter unit 106) comprising one or more transmitter contacts (e.g., transmitter contacts 244A) electrically contacting the one or more base contacts. The method 1100 includes, in 1106, coupling the base unit and the transmitter unit together, wherein the one or more transmitter contacts electrically contact the one or more base contacts in response to the base unit and the transmitter unit being coupled together.

The foregoing description discloses only example embodiments. Modifications of the above-disclosed apparatus and methods which fall within the scope of this disclosure will be readily apparent to those of ordinary skill in the art.

What is claimed is:

1. A base unit of a wearable device of a continuous analyte monitoring system, comprising:
   a cup configured to receive a power source, the cup comprising:
     one or more spring contacts; and
     a rim at least partially encircling the cup,
       wherein the one or more spring contacts and the rim are configured to secure the power source within the cup;
   a first power source contact at least partially located in the cup and configured to electrically contact a first terminal of the power source in response to the power source being received in the cup; and
   at least one base contact electrically coupled to the first power source contact, the at least one base contact configured to electrically contact at least one transmitter contact of a transmitter unit in response to the transmitter unit and the base unit being coupled together.

2. The base unit of claim 1, comprising a second power source contact at least partially located in the cup, wherein the second power source contact is configured to electrically contact a second terminal of the power source in response to the power source being received in the cup.

3. The base unit of claim 1, comprising the power source received in the cup.

4. The base unit of claim 3, wherein the power source is configured to remain functional after exposure to electron beam sterilization.

5. The base unit of claim 3, wherein the power source is radiation hardened.

6. The base unit of claim 3, wherein the power source is configured to remain functional after being exposed to an electron beam sterilization level of at least 25 KGy.

7. The base unit of claim 3, wherein the transmitter unit applies a force to the power source in response to the base unit and the transmitter unit being coupled together.

8. The base unit of claim 3, comprising an encapsulant covering at least a portion of the power source.

9. The base unit of claim 1, wherein the one or more spring contacts are configured to electrically contact the power source.

10. The base unit of claim 9, wherein the rim fully encircles the cup.

11. The base unit of claim 9, wherein the one or more spring contacts are configured to force the power source to the rim.

12. The base unit of claim 1, comprising a tube through the base unit, the tube configured to receive a sensor, the sensor configured to be located subcutaneously.

13. The base unit of claim 12, wherein the at least one base contact comprises a plurality of base contacts at least partially encircling the tube.

14. The base unit of claim 12, wherein the tube is configured to secure the transmitter unit to the base unit.

15. The base unit of claim 1, comprising a base retainer ring located proximate a perimeter of the base unit, the base retainer ring having one or more openings configured to engage with one or more tabs on the transmitter unit to couple the base unit and the transmitter unit together.

16. A wearable device of a continuous analyte monitoring system, comprising:
a base unit, the base unit comprising:
a cup configured to receive a battery, the cup comprising:
one or more spring contacts; and
a rim at least partially encircling the cup,
wherein the one or more spring contacts and the rim are configured to secure the battery within the cup;
a battery contact at least partially located in the cup and configured to electrically contact a terminal of the battery in response to the battery being received in the cup; and
at least one base contact electrically coupled to the battery contact; and
a transmitter unit configured to couple to the base unit, the transmitter unit comprising:
a recess configured to at least partially receive the battery in response to the transmitter unit and the base unit being coupled together, the battery supplying all power to the transmitter unit,
wherein the at least one base contact of the base unit is configured to electrically contact at least one transmitter contact of the transmitter unit in response to the transmitter unit and the base unit being coupled together.

17. The wearable device of claim 16, comprising a hole configured to receive a tube attached to the base unit in response to the transmitter unit and the base unit being coupled together.

18. The wearable device of claim 17, comprising one or more contacts arranged around the hole and configured to conduct current from the battery to the transmitter unit.

19. The wearable device of claim 16, further comprising a contact configured to contact the terminal of the battery in the base unit in response to the transmitter unit and the base unit being coupled together.

20. A wearable device of a continuous analyte monitoring system, comprising:
a base unit comprising:
a cup;
a power source received in the cup, the cup comprising:
one or more spring contacts configured to electrically contact the power source; and
a rim at least partially encircling the cup,
wherein the one or more spring contacts and the rim are configured to secure the power source within the cup;
a power source contact at least partially located in the cup and electrically contacting a terminal of the power source;
one or more base contacts electrically coupled to the power source contact; and
a transmitter unit comprising one or more transmitter contacts electrically contacting the one or more base contacts.

21. The wearable device of claim 20, wherein the transmitter unit applies a force to the power source in response to coupling the base unit and the transmitter unit together.

22. The wearable device of claim 20, further comprising a transmitter contact contacting the terminal of the power source.

23. The wearable device of claim 20, comprising a sensor configured to be located subcutaneously.

24. A method of manufacturing a base unit of a wearable device of a continuous analyte monitoring system:
forming a cup comprising:
one or more spring contacts; and
a rim at least partially encircling the cup,
wherein the cup is configured to receive a power source such that the one or more spring contacts and the rim of the cup are configured to secure the power source within the cup;
locating a power source contact at least partially in the cup, the power source contact configured to electrically contact a terminal of the power source in response to the power source being received in the cup; and
electrically coupling at least one base contact with the power source contact, the at least one base contact configured to electrically contact at least one transmitter contact of a transmitter unit in response to the transmitter unit and the base unit being coupled together.

25. A base unit of a wearable device of a continuous analyte monitoring system, comprising:
a tube configured to receive an insertion tool, the insertion tool configured to attach a biosensor to a user;
at least one power source contact configured to electrically contact at least one terminal of a power source;
a cup configured to receive the power source, the cup comprising:
one or more spring contacts; and
a rim at least partially encircling the cup, wherein the rim and the one or more spring contacts are configured to secure the power source within the cup; and at least one base contact electrically coupled to the at least one power source contact, the at least one base contact arranged around a perimeter of the tube and configured to contact at least one transmitter conductor of a transmitter unit in response to the base unit and the transmitter unit being coupled together.

26. A method of using a wearing device of a continuous analyte monitoring system, comprising:

providing a base unit comprising:
- a cup comprising a rim and one or more spring contacts;
- a power source received in the cup, wherein the power source is secured within the cup by the rim and the one or more spring contacts;
- a power source contact at least partially located in the cup and electrically contacting a terminal of the power source; and
- one or more base contacts electrically coupled to the power source contact;

providing a transmitter unit comprising one or more transmitter contacts; and coupling the base unit and the transmitter unit together, wherein the one or more transmitter contacts electrically contact the one or more base contacts in response to the base unit and the transmitter unit being coupled together.

* * * * *